United States Patent [19]

Duranleau et al.

[11] Patent Number: 4,602,085

[45] Date of Patent: Jul. 22, 1986

[54] CATALYTIC PROCESS FOR THE PRODUCTION OF HYDROXYAMINE DERIVATIVES OF ALPHA METHYL GLUCOSIDE

[75] Inventors: Roger G. Duranleau, Georgetown; Michael E. Brennan, Austin, both of Tex.

[73] Assignee: Texaco Inc., White Plains, N.Y.

[21] Appl. No.: 642,309

[22] Filed: Aug. 20, 1984

[51] Int. Cl.$^4$ .................. C07H 17/04; C07H 15/04
[52] U.S. Cl. .................. 536/17.2; 536/4.1; 536/18.3; 536/18.6; 536/120
[58] Field of Search .................. 536/4.1, 17.2, 17.9, 536/18.3

[56] References Cited

U.S. PATENT DOCUMENTS

| | | | |
|---|---|---|---|
| 3,128,311 | 4/1964 | Shirley et al. | 260/585 |
| 3,152,998 | 10/1964 | Moss | 252/470 |
| 3,255,253 | 6/1966 | Kuryla | 536/17.2 |
| 3,390,184 | 6/1968 | Moss et al. | 260/585 |
| 3,445,525 | 5/1969 | Bormann et al. | 536/18.3 |
| 3,654,370 | 4/1972 | Yeakey | 260/584 |
| 3,838,076 | 9/1974 | Moss et al. | 260/2.5 |
| 4,014,933 | 3/1977 | Boettger et al. | 260/563 |
| 4,122,253 | 10/1978 | Watts, Jr. et al. | 536/50 |
| 4,153,581 | 5/1979 | Habermann | 252/472 |
| 4,166,172 | 8/1979 | Klein | 536/4 |

FOREIGN PATENT DOCUMENTS

| | | | |
|---|---|---|---|
| 0017651 | 10/1980 | European Pat. Off. | 536/4.1 |
| 1530570 | 11/1978 | United Kingdom | 536/4.1 |

*Primary Examiner*—Johnnie R. Brown
*Attorney, Agent, or Firm*—Jack H. Park; Kenneth R. Priem

[57] ABSTRACT

It has been discovered in accordance with the present invention that oxyalkylated derivatives of alkyl glucosides can be effectively reductively aminated by bringing the oxyalkylated alkyl glucoside feedstock into contact with a reductive amination catalyst in the presence of ammonia and hydrogen to provide derivatives containing both hydroxyl groups and amine groups. These derivatives are useful, for example, as gas scrubbing agents, raw materials for the preparation of corrosion inhibitors, epoxy curing agents, raw materials for the preparation of surfactants and as polyols for use in the preparation of polyurethanes.

4 Claims, No Drawings

CATALYTIC PROCESS FOR THE PRODUCTION OF HYDROXYAMINE DERIVATIVES OF ALPHA METHYL GLUCOSIDE

BACKGROUND OF THE INVENTION

1. Field of the Invention

This invention relates to an improved process for the production of hydroxyamines from oxyalkylated alpha methyl glucoside. More particularly, this invention relates to a catalytic process for the conversion of oxyalkylated alkyl methyl glucoside feedstocks to products useful as gas scrubbing agents, epoxy resin curatives, polyurethane precursors, etc., wherein the feedstock is brought into contact with a reductive amination catalyst in the presence of about 1 to about 200 moles of ammonia per mole of feedstock and about 0.1 to about 50 mole of hydrogen per mole of feedstock at a temperature within the range of about 120° to about 250° C. and a pressure within the range of about 200 to about 5000 psig.

2. Prior Art

Watts et al. U.S. Pat. No. 4,122,253 discloses the reductive amination of starch derivatives. For example, a starch oxidized with an oxidizing agent such as sodium hypochlorite (i.e., a so-called "dialdehyde" starch) is reductively aminated with a dialkyl amine in the presence of a reductive amination catalyst and hydrogen. Watts et al. teach that known reductive amination catalysts such as those including one or more of the metals copper, nickel, cobalt, chromium, aluminum, manganese, platinum, palladium and rhodium and the oxides of these metals may be used. Additional nonreducible metal oxides such as chromium oxide, molybdenum oxide and manganese oxide may also be included in the catalyst compositions.

In Klein U.S. Pat. No. 4,166,172, a process is disclosed wherein a polyhydric initiator such as sucrose is reacted with ammonia in the presence of an alkylene oxide such as ethylene oxide or propylene oxide. In an example, an aqueous solution of sucrose to which ammonia had been added with pressure was reacted with ethylene oxide and then with propylene oxide to give a polyol product useful as a raw material in the manufacture of polyurethanes.

A wide variety of reductive amination catalysts are known. For example, Moss U.S. Pat. No. 3,152,998 discloses a nickel, copper, chromia catalyst. Habermann U.S. Pat. No. 4,153,581 discloses reductive amination catalysts comprising cobalt, copper and a third component selected from the group consisting of iron, zinc, zirconium and mixtures thereof. Boettger et al. U.S. Pat. No. 4,014,933 discloses the use of a cobalt, nickel and copper catalyst. British Pat. No. 1,530,570 discloses that reductive amination catalysts (hydrogenations/dehydrogenation catalysts) can suitably be prepared from cobalt, nickel, chromium, copper, manganese, molybdenum, palladium, platinum and rhodium and that such catalysts may contain mixtures of such metals.

SUMMARY OF THE INVENTION

It has been discovered in accordance with the present invention that oxyalkylated derivatives of alkyl glucosides can be effectively reductively aminated by bringing the oxyalkylated alkyl glucoside feedstock into contact with the reductive amination catalyst in the presence of ammonia and hydrogen to provide derivatives containing both hydroxyl groups and amine groups. These derivatives are useful, for example, as gas scrubbing agents, raw materials for the preparation of corrosion inhibitors, as epoxy curing agents, as raw materials for the preparation of surfactants and as polyols for use in the preparation of polyurethanes.

DETAILED DESCRIPTION

Starting Materials

The starting materials for the present invention are an oxyalkylated alkyl glucoside which has been reacted with from about 3 to about 10 moles of propylene oxide or ethylene oxide or a mixture thereof. The other starting materials include ammonia, hydrogen and a reductive amination catalyst.

The alkoxylated alkyl glucoside feedstocks are known materials which can be prepared by reacting an alkyl glucoside with an alkylene oxide such as ethylene oxide or propylene oxide under basic conditions. Thus, for example, ethylene oxide and/or propylene oxide may be reacted with an alkyl glucoside, such as a $C_1$–$C_4$ alpha alkyl glucoside (e.g., alpha methyl-, alpha ethyl-, alpha propyl-, alpha butyl-, etc. glucoside) or a corresponding beta-D-glucopyranoside (e.g., beta methyl-, beta ethyl-, beta propyl-, beta butyl-, etc. D-glucopyranoside).

Reductive Amination of Alkoxylated Alpha Methyl Glucoside Feedstocks

It has been discovered in accordance with the present invention both that it is necessary to use comparatively rigorous reductive amination conditions in order to convert at least a portion of the hydroxyl groups on the alkoxylated feedstock to amine groups and that the glucoside ring is retained when the reaction conditions include the use of a temperature within the range of about 120° to 250° C. and a pressure within the range of about 200 to about 5000 psig. Under these conditions, products having from about 40 to about 85% of the original hydroxyl groups converted to the corresponding amino groups are readily obtained with good selectivity.

The process of the present invention is suitably conducted in the presence of about 1 to about 200 moles of ammonia per mole of oxyalkylated alkyl glucoside feedstock. Preferably, from about 4 to about 130 moles of ammonia per mole of oxyalkylated alkyl glucoside feedstock are used.

Hydrogen is also a necessary feed component for the present invention. Suitably, from about 0.1 to about 50 moles of hydrogen per mole of oxyalkylated alyl glucoside feedstock is employed. More preferably, from about 1 to about 25 moles of hydrogen per mole of oxyalkylated alkyl glucoside feedstock is employed.

The reaction is suitably conducted under comparatively moderate pressure conditions of about 200 to about 5000 psig.

It is of importance to the present invention to use a comparatively narrow temperature range of about 120° to about 250° C. under the aforesaid other reaction conditions if the desired selectivity and yield are to be obtained.

The process of the present invention may be conducted batchwise using an autoclave containing powdered catalyst, or it may be conducted continuously by passing the feed materials over a bed of pelleted catalyst. When the process of the present invention is conducted continuously, the desired molar ratios of ammonia and hydrogen to feedstock can be established and maintained by regulating the rates at which the feed components are fed to the reactor.

The reaction mixture formed as a result of the reductive amination of the feedstock may be recovered in any suitable manner, such as by vacuum stripping, to obtain the desired primary amine as a bottoms product.

Any suitable metallic reductive amination catalyst may be used such as those disclosed by British Pat. No. 1,530,570, Moss et al., Boettger, Habermann, etc. The preferred class of reductive amination catalysts are nickel, copper, chromia catalysts of the type disclosed in Moss U.S. Pat. No. 3,152,998.

DETAILED DESCRIPTION OF THE PREFERRED EMBODIMENT OF THE PRESENT INVENTION

The present invention is further illustrated by the following specific examples which are given by way of illustration and which are not intended as limitations on the scope of this invention.

EXAMPLE 1 (5677-54)

A sample of a 5.5 molar adduct of propylene oxide (PO) and alpha methyl glucoside (methyl-α-D-glucopyranoside) was passed, along with hydrogen and ammonia over a nickel based catalyst. The adduct had a hydroxyl number of 441 and therefore an average molecular weight of 512. This adduct (Olin Poly G440) was commercially available, but similar materials are readily prepared by condensation of alpha methyl glucoside and the proper amount of PO. The catalyst was a commercial nickel, copper and chromia catalyst and 500 cc. of pellets were used. The flow rates of the components were: Ammonia =0.72 lbs/hr, adduct=0.22 lbs/hr and $H_2$=70 liters/hr all in an upflow mode. Temperatures were varied to demonstrate the optimum conversion and selectivity of this amination reaction. The pressure was held steady at 2700 psig. The lhsv of the system was about 1.0 (0.94 lbs/hr=500 cc/hr). The reactant flows were started, conditions brought to equilibrium and the system run for 3-4 hours to allow the product stream to reach a constant composition. The product was then collected for a 2 hour period after which new conditions were established and the process repeated at the temperature of interest. Each product was stripped of $NH_3$ under vacuum (15-30 mm Hg) at 100° C. and analyzed for amine and hydroxyl content by standard titration methods. The products were also analyzed by NMR. Table I shows the results obtained. Conversion of the hydroxyl group ranged from 67 to 85%. The NMR analyses clearly showed the products had retained the methyl glucoside portions of the molecule as evidenced by the presence of the $CH_3O$ band which is present in both product and starting material.

EXAMPLE 2 5677-57

An adduct of alpha methyl glucoside and PO (7.0 moles) was treated as in Example 1. The flows of glucoside adduct was 0.25 lbs/hr and of $NH_3$ was 0.69 lbs/hr. Temperatures of 210°, 225°, and 235° C. were used. The results are shown in Table II, which show that hydroxyl group conversion ranged from 56-78% and primary amine content ranged from 79.3 to 86.6% of total amine.

EXAMPLE 3 5677-58

An adduct of alpha methyl glucoside and PO (4.0 moles) was treated as in Example 1. The flows of $NH_3$ and adduct were respectively, 0.75 and 0.19 lbs/hr. Runs were conducted at 210°, 225° and 235° C. The results are shown in Table III which indicate that hydroxyl group conversion to amino function ranged from 45.4-64.4% and primary amine content ranged from 69.3 to 84% of total amine.

TABLE I

| | Reductive Amination of α-Methylglucoside × 5.5 PO* | | | | | | | |
|---|---|---|---|---|---|---|---|---|
| Temp. °C. | % Yield | Total Acet. meq/g | Total Amine meq/g | 1° Amine meq/g | 2° + 3° Amine meq/g | % Conversion | % OH groups Converted | % of Amine in 1° Form | Mol. Wt. (calc.) |
| 210 | 97.4 | 6.66 | 4.46 | 4.05 | 0.41 | 100 | 67 | 90.8 | 600 |
| 225 | 87.1 | 6.66 | 5.25 | 4.32 | 1.03 | 100 | 80 | 80.7 | 600 |
| 235 | 74.0 | 6.44 | 5.74 | 3.91 | 1.83 | 100 | 89 | 68.1 | 621 |

TABLE II

| | Reductive Amination of α-Methylglucoside × 7.0 PO* | | | | | | | |
|---|---|---|---|---|---|---|---|---|
| Temp. °C. | % Yield | Total Acet. meq/g | Total Amine meq/g | 1° Amine meq/g | 2° + 3° Amine meq/g | % Conversion | % OH groups Converted | % of Amine in 1° Form | Mol. Wt. (calc.) |
| 210 | 99.4 | 6.36 | 3.58 | 2.84 | 0.74 | 100 | 56.2 | 79.3 | 629 |
| 225 | 98.9 | 6.12 | 3.66 | 3.17 | 0.49 | 100 | 60 | 86.6 | 654 |
| 235 | 93.0 | 5.88 | 4.56 | 3.72 | 0.84 | 100 | 78 | 81.6 | 680 |

*Conditions: lhsv = 1, upflowmode; $NH_3$/OH = 25/1; $H_2$ flow = 70 l/hour; Pressure = 2700 psig.

TABLE III

| | Reductive Amination of α-Methylglucoside × 4.0 PO* | | | | | | | |
|---|---|---|---|---|---|---|---|---|
| Temp. °C. | % Yield | Total Acet. meq/g | Total Amine meq/g | 1° Amine meq/g | 2° + 3° Amine meq/g | % Conversion | % OH groups Converted | % of Amine in 1° Form | Mol. Wt. (calc.) |
| 210 | 94.3 | 7.73 | 3.51 | 2.96 | 0.55 | 100 | 45.4 | 84 | 517 |
| 225 | 90.3 | 8.01 | 4.92 | 4.02 | 0.90 | 100 | 61.4 | 81.7 | 500 |
| 235 | 82.1 | 8.25 | 5.31 | 3.68 | 1.63 | 100 | 64.4 | 69.3 | 485 |

*Conditions: lhsv = 1, upflowmode; $NH_3$/OH = 25/1; $H_2$ flow = 70 lhour; Pressure = 2700 psig.

Having thus described our invention, what is claimed is:

1. An amine derivative of alpha methyl glucoside propoxylated with from about 3 to about 7 moles of propylene oxide per mole of alpha methyl glucoside, said derivative having been prepared by reductively aminating said propoxylated alpha methyl glucoside in the presence of a reductive amination catalyst and in the presence of about 1 to 25 moles of hydrogen and about 4 to about 30 moles of ammonia per mole of said propoxylated alpha methyl glucoside at a temperature within the range of about 210° to about 235° C. and a pressure within the range of about 200 to about 5000 psig. whereby from about 45 to about 90% of the original OH groups of the propoxylated alpha methyl glucoside are converted to $NH_2$ groups, of which amine groups, about 70 to about 90% are primary amine groups.

2. A product as in claim 1, wherein the propoxylated alpha methyl glucoside is a 5.5 molar adduct of propylene oxide and alpha methyl glucoside.

3. A product as in claim 1, wherein the propoxylated alpha methyl glucoside is a 7 molar propylene oxide adduct of alpha methyl glucoside.

4. A product as in claim 1, wherein the propoxylated alpha methyl glucoside is a 4 molar propylene oxide adduct of alpha methyl glucoside.

* * * * *